United States Patent
Freeman et al.

(10) Patent No.: US 9,567,366 B2
(45) Date of Patent: Feb. 14, 2017

(54) WATER-BASED PROLAMIN COMPOSITIONS, METHODS OF MAKING WATER-BASED PROLAMIN COMPOSITIONS, AND APPLICATIONS THEREOF

(75) Inventors: Leif Sedgewick Freeman, Sioux Falls, SD (US); John Warren Lawton, Jr., Sioux Falls, SD (US); Marvin Lynn Mitchell, Parker, CO (US); Melvin Glenn Mitchell, Penrose, NC (US)

(73) Assignee: POET RESEARCH, INC., Sioux Falls, SD (US)

( * ) Notice: Subject to any disclaimer, the term of this patent is extended or adjusted under 35 U.S.C. 154(b) by 337 days.

(21) Appl. No.: 13/548,839

(22) Filed: Jul. 13, 2012

(65) Prior Publication Data

US 2013/0014673 A1    Jan. 17, 2013

Related U.S. Application Data

(60) Provisional application No. 61/572,410, filed on Jul. 14, 2011.

(51) Int. Cl.
| | | |
|---|---|---|
| *C07K 1/14* | (2006.01) | |
| *C08J 3/05* | (2006.01) | |
| *C09D 189/00* | (2006.01) | |
| *C07K 14/425* | (2006.01) | |

(52) U.S. Cl.
CPC ............. *C07K 1/145* (2013.01); *C07K 14/425* (2013.01); *C08J 3/05* (2013.01); *C09D 189/00* (2013.01)

(58) Field of Classification Search
None
See application file for complete search history.

(56) References Cited

U.S. PATENT DOCUMENTS

| | | | |
|---|---|---|---|
| 2,185,124 A | 12/1939 | Coleman | |
| 2,360,081 A | 10/1944 | Stewart | |
| 2,377,237 A | 5/1945 | James | |
| 2,545,656 A | 3/1951 | Dunne | |
| 2,657,148 A | 10/1953 | Ehrlich | |
| 2,810,656 A | 10/1957 | McDowell | |
| 5,021,248 A | 6/1991 | Stark et al. | |
| 5,182,130 A | 1/1993 | Haralampu et al. | |
| 5,254,673 A * | 10/1993 | Cook et al. | 530/373 |
| 5,324,351 A | 6/1994 | Oshlack et al. | |
| 5,580,959 A * | 12/1996 | Cook et al. | 530/373 |
| 5,705,207 A * | 1/1998 | Cook et al. | 426/89 |
| 7,737,200 B2 * | 6/2010 | Jabar et al. | 524/18 |
| 2005/0287248 A1 | 12/2005 | Jabar, Jr. et al. | |
| 2010/0178675 A1 | 7/2010 | Lawton, Jr. et al. | |
| 2011/0143013 A1 * | 6/2011 | Lawton, Jr. | 426/656 |

OTHER PUBLICATIONS

Esen, Asim, "Separation of Alcohol-Soluble Proteins (Zeins) from Maize into Three Fractions by Differential Solubility", Plant Physiol. 80: (1986) p. 623-627.

(Continued)

*Primary Examiner* — Melissa Swain
(74) *Attorney, Agent, or Firm* — Edna Vassilovski

(57) ABSTRACT

The invention relates to water-based prolamin (e.g., zein) compositions and to methods of making water-based prolamin compositions. The compositions may be used in paints, printing inks, varnishes, adhesives, glues, binders (e.g., for paper), food coatings, and the like.

25 Claims, 3 Drawing Sheets

(56) References Cited

OTHER PUBLICATIONS

Esen, Asim, "A Proposed Nomenclature for the Alcohol-soluble Proteins (Zeins) of Maize (*Zea mays* L.)", Journal of Cereal Science 5: (1987) p. 117-128.
Lawton, J. et al., "Chapter 9—Proteins of the Kernel", Corn: Chemistry and Technology, $2^{nd}$ edition, (2003) p. 313-354.
Shewry, P. et al., "Review Article—The prolamin storage proteins of cereal seeds: structure and evolution", Biochem. J. 267: (1990) p. 1-12.
Swallen, L.C., "Zein—A New Industrial Protein", Industrial and Engineering Chemistry 33, No. 3: (1941) p. 394-398.

\* cited by examiner

WATER-BASED PROLAMIN COMPOSITIONS, METHODS OF MAKING WATER-BASED PROLAMIN COMPOSITIONS, AND APPLICATIONS THEREOF

CROSS-REFERENCE TO RELATED APPLICATIONS

This application claims the benefit of U.S. application Ser. No. 61/572,410, filed Jul. 14, 2011, and entitled "WATER-BASED PROLAMIN COMPOSITIONS, METHODS OF MAKING WATER-BASED PROLAMIN COMPOSITIONS, AND APPLICATIONS THEREOF", the disclosure of which is incorporated herein by reference.

BACKGROUND

Prolamins are a class of plant proteins (e.g., zein from corn) that are high in prolamin and glutamine but are deficient in polar amino acids. Because of this deficiency, prolamins are difficult to maintain in an aqueous environment. Typically, prolamins (e.g., zein) are soluble in aqueous alcohol and/or ketone solutions, for example, about 40% to about 95% weight alcohol and/or ketone at room temperature.

The use of zein as the solid in coating compositions has been limited by its solubility properties. Zein is soluble in aqueous alcohol and/or ketone solutions, for example, about 40% to about 95% weight alcohol and/or ketone at room temperature. The use of organic solvents in the preparation of polymer coating formulations is viewed as a disadvantage as the formulations may have problems with flammability, carcinogenicity, and safety in use. Additionally, the use of organic solvents may not be favored due to environmental concerns. In view of the foregoing, what is desired is a method for preparing a flowable liquid composition for delivering a prolamin (e.g., zein), where the liquid portion of the flowable composition comprises primarily water, and does not include an appreciable amount of an organic solvent.

SUMMARY

The invention relates to water-based prolamin compositions and to methods of making water-based prolamin compositions. Also described are representative applications of the water-based prolamin compositions of the invention.

In one aspect, the invention relates to a method of making a water-based prolamin composition, the method comprising the steps of: (a) providing an acidified prolamin solution comprising: a prolamin; water; alcohol and/or ketone; and acid; and (b) removing at least a portion of the alcohol and/or ketone from the acidified prolamin solution to form the water-based prolamin composition.

In many embodiments, the prolamin comprises zein, gliadin, glutenin, hordein, secalin, avenin, gluten, kafirin, or mixtures thereof. When zein is used, the prolamin comprises α-zein and may further include at least one of β-zein or γ-zein. In many embodiments, the zein composition comprises α-zein, β-zein, and γ-zein.

When the water-based prolamin composition is in the form of a solution, the zein composition typically comprises, for example, about 56% to about 100% weight α-zein, and about 0% to about 44% weight combined β-zein and γ-zein. In other embodiments, the zein composition may comprises about 83% to about 100% weight α-zein, and about 0% to about 17% weight combined β-zein and γ-zein.

When the water-based prolamin composition is in the form of an emulsion, the zein composition typically comprises, for example, about 56% to about 88% weight α-zein, and about 12% to about 44% weight combined β-zein and γ-zein. In other embodiments, the zein composition may comprise about 75% to about 85% weight α-zein, and about 15% to about 25% weight combined β-zein and γ-zein.

In some embodiments, the step of providing an acidified prolamin solution (i.e., step (a)) comprises the steps of: (1) providing a prolamin solution comprising: a zein composition comprising: α-zein and at least one of β-zein or γ-zein; alcohol and/or ketone; and water; and (2) combining the prolamin solution with an acid to form the acidified prolamin solution.

In some embodiments, the step of providing a prolamin solution (i.e., step (1)) comprises the steps of: (A) providing a solvent composition comprising: alcohol and/or ketone, and water; and (B) combining the solvent composition with a zein composition comprising: α-zein and at least one of β-zein or γ-zein to form the prolamin solution. In other embodiments, the step of providing a prolamin solution (i.e., step (1)) comprises the steps of: (A) providing a composition comprising alcohol and/or ketone, water, and distillers' grain; (B) extracting prolamin from the distillers' grain to provide an extracted composition comprising prolamin, alcohol and/or ketone, and water; and (C) separating the distillers' grain from the extracted composition.

In other embodiments, the step of providing an acidified prolamin solution (i.e., step (a)) comprises the steps of: (1) providing an acidified solvent composition comprising: alcohol and/or ketone, water, and an acid; and (2) combining the acidified solvent composition with a zein composition comprising: α-zein and at least one of β-zein or γ-zein to form the acidified prolamin solution.

In many embodiments, the removing step (step (b)) comprises distilling at least a portion of the alcohol from the acidified zein solution. In some embodiments, the distillation comprises vacuum distillation.

In some embodiments, the acid comprises an organic acid (e.g., carboxylic acid), an inorganic acid, or a mixture thereof. Representative carboxylic acids include acetic acid, lactic acid, formic acid, propionic acid, glycolic acid, D-gluconic acid, and L-ascorbic acid. Examples of polycarboxylic acids include citric acid, malic acid, levulinic acid, tartaric acid, succinic acid, glutaric acid, isocitric acid, aconitic acid, and propane 1,2,3-tricarboxylic acid. Representative inorganic acids include hydrochloric acid (HCl).

In some embodiments, the alcohol and/or ketone is selected from methanol, ethanol, 1-propanol, 2-propanol, butanol (e.g., t-butanol), acetone, and mixtures thereof.

In another aspect, the invention provides a water-based prolamin composition comprising: water, a prolamin; an acid; about 35% weight or less alcohol and/or ketone; wherein the water-based zein composition has a pH of less than about 7 (e.g., about 2 to about 4).

In some embodiments, the acid comprises a carboxylic acid, and at least a portion of the carboxylic acid reacts with the alcohol to form an ester.

In some embodiments, the water-based composition comprises about 8% to about 35% weight zein; about 30% to about 75% weight water; about 0.1% to about 35% weight acid; and about 3% weight to about 35% weight alcohol and/or ketone.

In yet another aspect, the invention relates to a coating composition comprising a water-based prolamin composition as described herein. Examples of coating compositions include paints, printing inks, varnishes, adhesives, glues, binders, food coatings, and the like. In a specific embodiment, the invention relates to a paper sheet comprising a water-based prolamin composition of the invention. The water-based prolamin composition may be a binder for the fibers of the paper sheet or it may be a surface coating applied to on one or more surfaces of the paper sheet.

DETAILED DESCRIPTION

Figure 1:
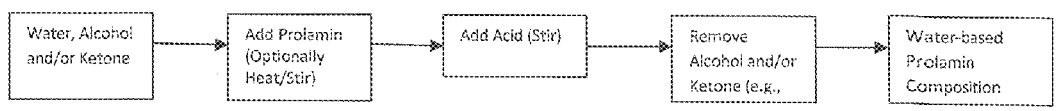
FIG. 1 is a process flow diagram illustrating an embodiment of a method of making a water-based prolamin composition according to the invention.

The invention relates to water-based prolamin (e.g., zein) compositions and to methods of making water-based compositions. The water-based compositions of the invention may be suitable, for example, for use in coatings (e.g., paints, varnishes, binders (e.g., for paper) and adhesives) among other applications.

The water-based compositions of the invention are prepared from starting materials including a prolamin composition (e.g., a zein composition), an acid (e.g., an organic acid (e.g., carboxylic acid) or inorganic acid), an alcohol and/or ketone (e.g., ethanol), and water. Each of the starting materials will be described in more detail below.

Prolamin

The invention relates broadly to water-based compositions prepared from prolamins. As used herein the term "prolamin" refers to a class of plant storage proteins found in cereal grains and that are characterized by having a high glutamine and proline content and their solubility in 70% aqueous alcohol. Examples of prolamins include zein (found in corn), gliadin and glutenin (found in wheat), hordein (found in barley), secalin (found in rye), avenin (found in oats), gluten (mixture of gliadin/glutenin from wheat), and kafirin (found in sorghum). Since prolamins are deficient in polar amino acids they are difficult to maintain in an aqueous environment.

One useful prolamin is zein. Zein comprises approximately 40% to 50% weight percent of the total protein in corn, or about 4% weight of the corn kernel. Zein exists in several forms including α-zein, β-zein, γ-zein, and δ-zein. Each form of zein has a different amino-acid profile and exhibits slightly different properties. α-Zein makes up about 70% weight of the zein in corn and is the major zein found in commercial zein. β-Zein makes up about 5% weight of the zein in corn. γ-Zein makes up about 20% to 25% weight of the zein in corn. δ-Zein accounts for about 1% to 5% weight of the zein in corn.

The forms and solubility properties of zein have been characterized, for example, in Lawton et al. "Chapter 9—Proteins of the Kernel." *Corn: Chemistry and Technology*, $2^{nd}$ edition. White et al. (Eds.). St. Paul, Minn.: American Association of Cereal Chemists, 2003. pp. 313 to 354; and in Esen, Asim. "A Proposed Nomenclature for the Alcohol-Soluble Proteins (Zeins) of Maize (*Zea mays* L.)."*Journal of Cereal Science* 5 (1987): 117-128, the disclosures of which are incorporated herein by reference. The various forms of zein may be characterized, for example, using molecular weight, solubility, and amino acid content. A brief summary of the characteristics of the various forms of zein are shown TABLE 1.

TABLE 1

| | Molecular Weight $(M_r)$ (kDa)* | Solubility | Amino Acid Profile |
|---|---|---|---|
| α-zein | 19, 22 | Soluble in 50-95% (v/v) propan-2-ol but insoluble in 30% propan-2-ol/30 mM Na ethanoate pH 6.0. | Devoid of lysine and low in basic amino acids; Rich in alanine and leucine. |
| β-zein | 15 | Soluble in 30-85% (v/v) propan-2-ol containing a reducing agent but insoluble in both 90% propan-2-ol and 30% propan-2-ol/30 mM Na ethanoate, pH 6.0. | Rich in cysteine and methionine |
| γ-zein | 16, 27, 50 | Soluble in 0-80% (v/v) propan-2-ol containing a reducing agent as well as in 30% propan-2-ol/30 mM Na ethanoate, pH 6.0. | Rich in proline and cysteine; low in lysine |
| δ-zein | 10, 18 | Soluble in 50-95% (v/v) propan-2-ol but insoluble in 30% propan-2-ol/30 mM Na ethanoate pH 6.0. | Rich in methionine |

*SDS-PAGE

Zein may be extracted from corn gluten meal, a by-product of the corn wet milling process. In a wet milling process, the kernel is fractionated by first steeping the kernels in water that contains sulfur dioxide, and then separating the kernels into endosperm, fiber, and germ. The endosperm is further processed to produce starch and corn gluten. Gluten can be dried to produce corn gluten meal. Corn gluten meal may comprise about 60% percent protein and is typically used as the starting material for zein extraction in commercial zein production. However, the sulfur dioxide (or other chemicals) used in the production of corn gluten meal may adversely affect the quality of the zein.

In some embodiments, zein is extracted from fermentation products of a corn dry milling process, for example, as described in U.S. Patent Application 2010/0178675 (Lawton et al.), the disclosure of which is incorporated herein by reference. As reported by Lawton, zein may be extracted from beer, wet cake, and DDG that result from ethanol processes including, for example, cooked starch fermentation, raw starch fermentation, and endosperm raw starch fermentation. Lawton et al. describes extracting the zein using ethanol in water (e.g., 40% to 90% weight ethanol) optionally including sodium hydroxide (e.g., 0 to 7.0% sodium hydroxide).

In an exemplary embodiment, the zein composition comprises α-zein, β-zein, and γ-zein. Extraction of β-zein and γ-zein along with α-zein is facilitated by the addition of a base (e.g., sodium hydroxide) in the extraction solvent. Other alkalis or reducing agents may be used to extract β-zein and γ-zein along with α-zein. In an exemplary embodiment, a useful zein composition may be obtained from DDG by extracting the DDG with 70% (w/w) aqueous ethanol. The solvent to solids ratio used is typically about 5:1, although other ratios may be useful. The 70% aqueous ethanol typically contains about 3.5% weight sodium hydroxide based on the amount of the dried DDG used for extraction. The DDG and 70% aqueous ethanol containing sodium hydroxide is typically stirred at about 70° C. for about 30 min. After the extraction, the mixture is neutralized to about pH 7 using hydrochloric acid. The mixture is then centrifuged to separate the solids from the liquid containing the zein. The zein solution can be purified by passing it through a 10,000 molecular weight cut-off ultrafiltration membrane. The purified zein solution can then be dried, for example, using a double drum vacuum dryer. In many embodiments, the resulting extracted zein composition comprises about 15% to about 23% weight combined β-zein and γ-zein with the remainder being α-zein.

In some embodiments, the zein composition comprises α-zein and may optionally comprise β-zein and γ-zein. The composition of the zein may vary, for example, depending upon the form of water-based zein composition that is desired (i.e., a solution or an emulsion). When a water-based zein solution is desired, the zein composition typically comprises about 56% to about 100% weight α-zein, and about 0% to about 44% weight combined β-zein and γ-zein. In an exemplary embodiment, the zein composition comprises about 83% to about 100% weight α-zein, and about 0% to about 17% weight combined β-zein and γ-zein.

When a water-based zein emulsion is desired, the zein composition typically comprises at least some amount of β-zein and/or γ-zein. Generally, as the amount of β-zein and/or γ-zein increases, the stability of the resulting emulsion also increases. In an exemplary embodiment, the zein composition comprises about 10% weight or greater combined β-zein and γ-zein, for example, about 12% or greater, about 14% weight or greater, or about 15% weight or greater combined β-zein and γ-zein. In some embodiments, the zein composition comprises about 56% to about 88% weight α-zein, and about 12% to about 44% weight combined β-zein and γ-zein. In an exemplary embodiment, the zein composition comprises about 75% to about 85% weight α-zein, and about 15% to about 25% weight combined β-zein and γ-zein.

Acid

The invention makes use of an acid to prepare the water-based zein compositions. Useful acids may be organic acids (e.g., carboxylic acids) or inorganic acids. Useful organic acids include carboxylic acids, for example, monocarboxylic acids or polycarboxylic acids. In many embodiments, the carboxylic acids fit the general formula R—(COOH)$_n$ where n ranges from about 1 to about 3; and where R is an n-functional organic radical. Useful carboxylic acids display at least partial solubility with water. Examples of monocarboxylic acids include acetic acid, lactic acid, formic acid, propionic acid, glycolic acid, D-gluconic acid, and L-ascorbic acid. Examples of polycarboxylic acids include citric acid, malic acid, levulinic acid, tartaric acid, succinic acid, glutaric acid, isocitric acid, aconitic acid, and propane 1,2,3-tricarboxylic acid. Useful inorganic acids include, for example, hydrochloric acid (HCl). Other acids or mixtures of acids may also be used. The amount of acid may be chosen based on various considerations. Typically, the amount of acid used provides a weight ratio ranging from about 1 part acid to about 4 parts zein (i.e., a 1:4 acid:zein weight ratio) up to about 1 part acid to about 1 part zein (i.e., a 1:1 acid:zein weight ratio). In some embodiments, an acid:zein weight ratio of greater than 1:1 (e.g., 1.25:1) may also be desirable.

In some embodiments, it may be desirable to adjust the acid content to achieve a particular property in the water-based zein composition. For example, citric acid may cause tackiness in the zein composition when it is dried. Therefore, increasing the citric acid content may be desirable for an adhesive application, whereas limiting the citric acid content may be desirable for a fast-drying coating application. In some embodiments, it may be desirable to add acid to achieve a desired pH in the resulting composition. For example, acid may be added to provide a pH of about 5 or less, for example, about 3 to about 4. As a general guide, in many embodiments, the acid is present in the initial composition (i.e., before removal of alcohol) in an amount up to about 12% weight, for example, from about 0.1% to about 11% weight.

Alcohol/Ketone

The invention makes use of an alcohol, ketone, or mixture thereof (i.e., an alcohol and/or ketone) to prepare the water-based zein compositions. Useful alcohols may contain one or more alcohol (i.e., —OH) groups and provide solubility for the zein. For example, useful alcohols may be monohydric alcohols or polyols. Typically, the alcohols fit the general formula R—(OH)$_n$ where n ranges from about 1 to about 4 (typically 1); and where R is an n-valent organic radical. In many embodiments, R is a short chain alkyl group typically having about 1 to about 4 carbon atoms. Representative examples of useful alcohols include methanol, ethanol, 1-propanol, 2-propanol, butanol (e.g., t-butanol), and the like or a mixture thereof. Useful ketones display at least some solubility in water and are solvents for prolamins when mixed with water. One representative example of a useful ketone is acetone.

The presence of an alcohol and/or ketone increases the solubility of the zein in the solvent composition (or acidified solvent composition) making it possible to dissolve the zein in the solvent composition (or acidified solvent composition). Typically, the amount of alcohol and/or ketone present is an effective amount to provide solubility of the zein in the solvent composition or acidified solvent composition. The solubility of zein in aqueous ethanol depends upon factors including pH, temperature, zein composition, among other factors. In some embodiments, at pH of 7 and at room temperature, an effective amount of ethanol ranges from about 50% to about 85% weight aqueous ethanol.

After removal (e.g., via distillation) of the alcohol and/or ketone, the amount of alcohol and/or ketone is reduced in the resulting water-based zein composition. For example, in many embodiments, the water-based zein composition comprises about 35% weight or less alcohol and/or ketone, for example, about 25% weight or less alcohol and/or ketone, about 20% weight or less alcohol and/or ketone, about 15% weight or less alcohol and/or ketone, or about 10% weight or less alcohol and/or ketone.

Water

Compositions of the invention are water-based compositions. As used herein, the term "water-based" refers to a solids-containing composition that is rendered flowable by a liquid phase that contains water. Water is typically present in the water-based zein compositions of the invention in an amount ranging from about 30% to about 75% weight of the composition although other amounts may be useful. Typically, distilled water is used to prepare the water-based zein compositions of the invention.

Method of Making Water-Based Prolamin Compositions

In one aspect, the invention provides a method of making a water-based prolamin composition, the method comprising the steps of: (a) providing an acidified prolamin solution comprising: a prolamin; water; alcohol and/or ketone; and acid; and (b) removing at least a portion of the alcohol and/or ketone from the acidified prolamin solution to form the water-based prolamin composition.

In some embodiments (see, FIG. 1), the acidified prolamin composition (see, step (a)) may be prepared by providing a solvent composition comprising water and alcohol and/or ketone, and then combining the solvent composition with prolamin. After combining with the prolamin, the resulting composition can be acidified by combining it with an acid to form the acidified prolamin composition.

Figure 2:
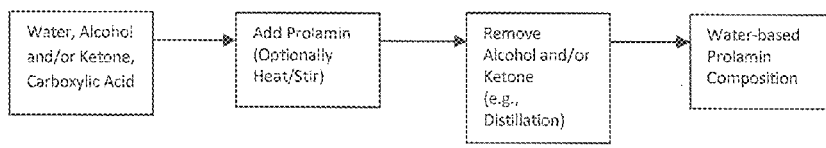
FIG. 2 is a process flow diagram illustrating an embodiment of a method of making a water-based prolamin composition according to the invention.

In other embodiments (see, FIG. 2), the acidified prolamin composition may be prepared by providing an acidified solvent composition comprising water, alcohol and/or ketone, and acid, and then combining the acidified solvent composition with prolamin to form the acidified prolamin composition.

Figure 3:
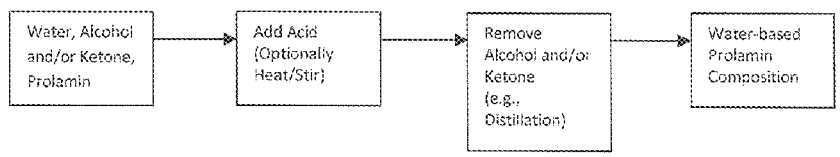
FIG. 3 is a process flow diagram illustrating an embodiment of a method of making a water-based prolamin composition according to the invention.

In yet other embodiments (see, FIG. 3), the acidified zein composition may be prepared by providing a composition comprising water, alcohol and/or ketone, and prolamin, and then adding an acid to provide the acidified prolamin composition.

In some embodiments, the solvent composition or acidified solvent composition may be heated (e.g., up to the boiling point of the composition) in order to assist dissolution of the prolamin. Typically, the solvent composition or acidified solvent composition is stirred to further assist dissolution of the prolamin.

In embodiments using a carboxylic acid, at least a portion of the alcohol may react with a portion of the carboxylic acid to form an ester compound. For example, 1 mole of citric acid may react with up to about 3 moles of ethanol to form an ethyl ester of citric acid (e.g., monoethyl citrate, diethyl citrate, or triethyl citrate). The formation of the ester acts to consume at least a portion of the alcohol in the composition.

Although not wishing to be bound by theory, it is also believed that heating the zein while in the solvent composition (i.e., in presence of alcohol and acid) may convert at least a portion of the glutamine that is present in the zein to glutamic acid. Because glutamic acid is water soluble, the conversion of glutamine to glutamic acid may increase the water solubility of the zein.

After dissolving the prolamin, a portion of the alcohol and/or ketone is then removed from the composition. The removal of the alcohol and/or ketone is typically accomplished by a distillation process where alcohol and/or ketone is distilled from zein composition in the form of a distillate. The distillation apparatus may include, for example, a heating source to apply heat to the zein solution, distillation column, and condenser. Vacuum distillation may optionally be employed. In some embodiments, when distilled from an acidified zein composition, the distillate comprises about 70% to about 85% weight ethanol, and about 15% to about 30% weight water.

Upon removal of the alcohol and/or ketone, the water-based prolamin composition is formed. Typically, the water-based prolamin composition comprises about 8% to about 35% weight prolamin; about 30% to about 75% weight water; about 0.1% to about 35% weight acid; and up to about 35% weight alcohol and/or ketone.

Figure 4:
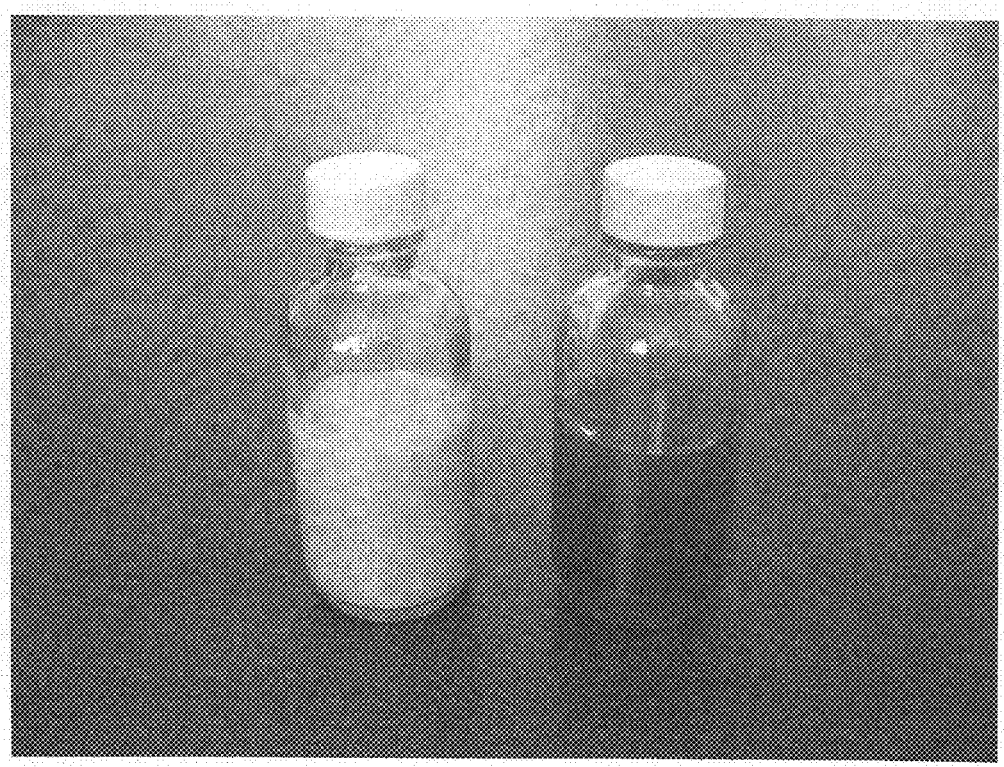
FIG. 4 is a photograph showing water-based prolamin compositions of the invention in emulsion (left) and solution (right) forms.

In many embodiments, the form of the water-based zein composition depends upon the amount of alcohol used in the starting composition. For example, when zein is the prolamin and ethanol is the alcohol, the resulting water-based zein solution may be in the form of an emulsion or may be in the form of a solution. When in emulsion form, the zein comprises the dispersed phase, and the liquid phase (i.e., water, alcohol and/or ketone, acid, and ester) comprises the continuous phase of the emulsion. Typically, the emulsion has a milky appearance similar, for example, to a latex emulsion. When in solution form, the zein is dissolved in a liquid phase (i.e., water, alcohol and/or ketone, acid, and ester) to provide a zein solution. The zein solutions are typically transparent colored liquids, for example, transparent yellow to brown liquids. An example of a typical emulsion is shown in FIG. 4 on the left of the picture. An example of a typical solution is shown in FIG. 4 on the right of the picture.

Typically, as the amount of alcohol and/or ketone in the water-based zein composition increases, a solution is favored over an emulsion. In general, an emulsion may be favored at a starting alcohol (e.g., ethanol) concentration of about 60% weight or less, and a solution may be favored at an alcohol (e.g., ethanol) concentration of about 70% weight or greater. When distilling a composition useful for forming an emulsion, the end point of the distillation can be defined when the composition turns from bright yellow to opaque. At this point, the heat source is removed and the emulsion is stirred while it is allowed to cool to room temperature. It has been observed that stirring the composition while cooling typically provides for a more stable emulsion (i.e., less likely to settle). In addition, it has been observed that agitating the emulsion periodically during the first few days after formation provides a more stable emulsion (i.e., less likely to settle). When distilling a composition useful for forming a solution, no dramatic color change from transparent to opaque is observed.

Between about 60% and about 70% weight alcohol, a less stable transition phase composition has been observed. Although the exact nature of this transition phase is not known, the transition phase does not appear to be either a typical solution or emulsion. Generally, upon being removed from heat, the transition phase composition turns opaque as it cools. After it cools, the transition phase composition typically appears either as a slightly opaque solution, a chunky emulsion, or a transparent yellow liquid top layer with a gelled yellow bottom layer.

In an exemplary embodiment of the method, water, ethanol, and citric acid are first combined in a vessel and are stirred together to form the acidified solvent composition. The acidified solvent composition is then optionally heated and stirred while zein is added to the composition. During the addition of the zein, the acidified solvent composition may be heated. In some embodiments, the addition of the zein takes place over a time period ranging from about 1 minute to about 10 minutes. After the zein has been added and dissolved in the acidified solvent composition, the ethanol is then removed by distillation from the composition. Typically, the distillation occurs at a temperature ranging from about 70° C. to about 100° C at atmospheric pressure.

Figure 3A:
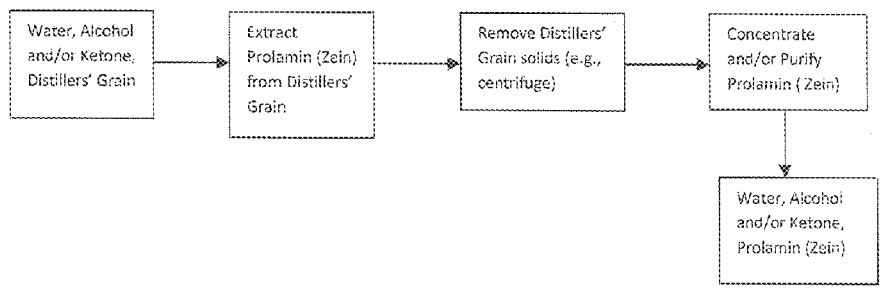
FIG. 3A is a process flow diagram illustrating an embodiment of a method of making a water-based prolamin composition according to the invention.

In another exemplary embodiment of the method, prolamin is extracted from distillers' grain into a solution comprising alcohol and/or ketone and water. This may occur, for example, appurtenant to a process for producing ethanol from corn. As shown in FIG. 3A, distillers' grain (e.g., from a corn ethanol process) is contacted with a solution comprising alcohol and/or ketone and water solution to extract the prolamine (e.g., zein) from the distillers' grain. Optionally, a reducing agent (e.g., base) may be added to facilitate extraction. After extraction of prolamin into the alcohol and/or ketone, the distillers' grain can be removed from the extraction slurry. Typically, this is accomplished by centrifugation although other techniques (e.g., filtration, screw press) may also be used. After removing the distillers' grain, the remaining solution containing prolamin, alcohol and/or ketone, and water can be treated in order to increase the concentration of prolamin. Examples of techniques used to concentrate and/or purify the zein include membrane separation, distillation, solvent evaporation, precipitation, and the like. After concentration and/or purification, the solution comprising prolamin, alcohol and/or ketone, and water can be used to prepare a water-based prolamin composition of the invention, for example, using the technique detailed in FIG. 3.

Figure 5:
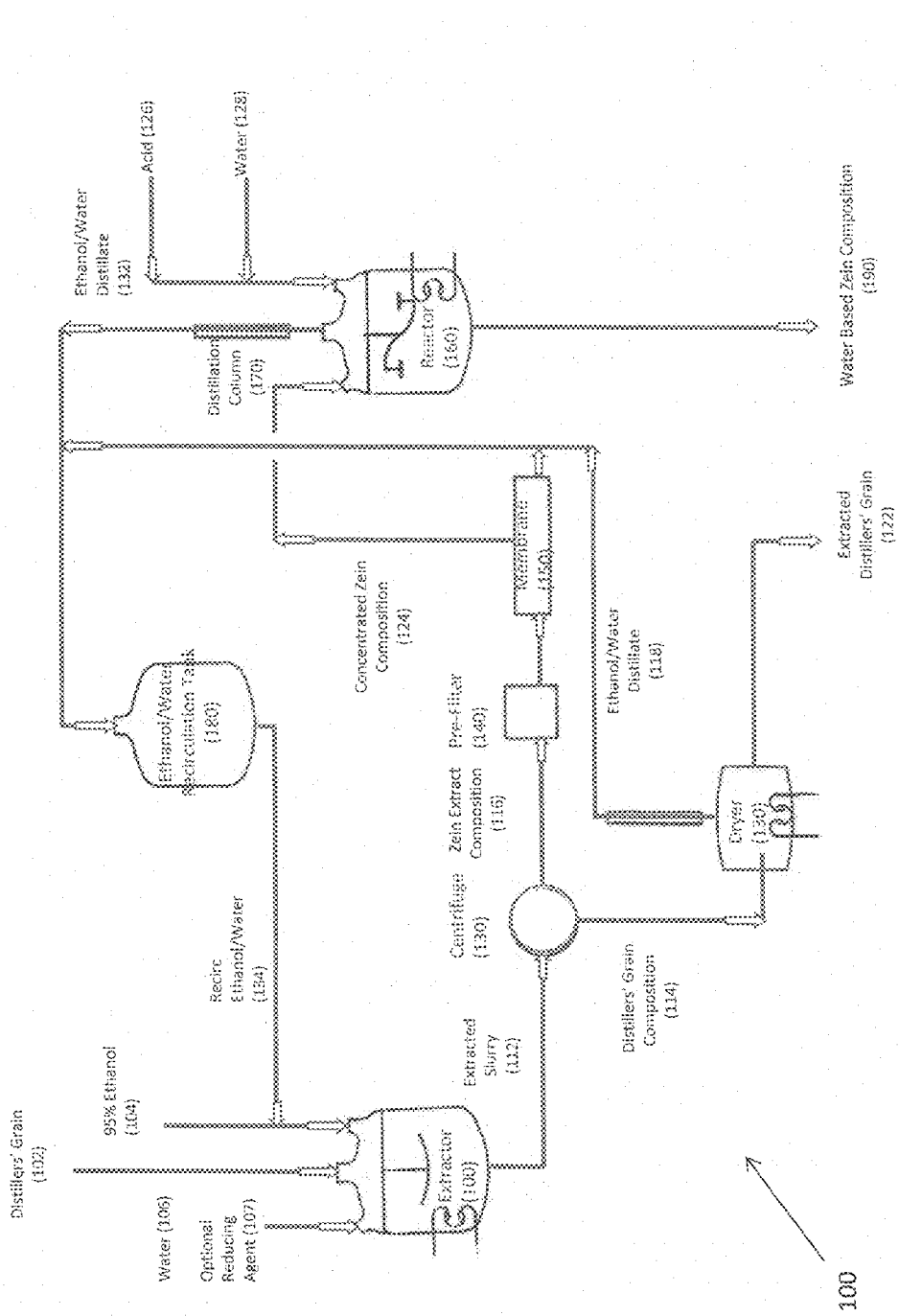
FIG. 5 is a process flow diagram illustrating an embodiment of a continuous method of making a water-based prolamin composition according to the invention.

Referring now to FIG. 5, an exemplary continuous process 100 for preparing a water-based zein composition of the invention is shown. As shown in FIG. 5, distillers' grain 102, ethanol 104 (e.g., 95% ethanol), water 106, and recirculated ethanol/water mixture 134 are fed into extractor 110. Optionally, a reducing agent 107 (e.g. a base) may be added to the extractor. In the extractor 110, zein is extracted from the distillers' grain 102 to form an extracted slurry composition 112. The extracted slurry composition 112 comprises zein, distillers' grain, ethanol, and water. The extracted slurry composition 112 is then fed to centrifuge 120 which separates the extracted slurry composition 112 into a distillers' grain composition 114 and a zein extract composition 116. The distillers' grain composition 114 is then fed to dryer 130 which dries off the ethanol and water to yield a dried extracted distillers' grain 122 and an ethanol/water distillate 118. From the centrifuge 120, zein extract composition 116 is fed through pre-filter 140 and membrane 150. Membrane 150 increases the concentration of the zein to form a concentrated zein composition 124. The concentrated zein composition 124 is then fed to reactor 160. Also supplied to reactor 160 is acid 126 and water 128. Reactor 160 is equipped with a heat source and distillation column 170 for distilling off a portion of the ethanol as ethanol/water distillate 132. The ethanol/water distillate 132 and the ethanol/water distillate 118 are combined and fed to ethanol/water recirculation tank 180 where the recirculated ethanol/water mixture 134 is stored for use in the process. In reactor 160, the concentrated zein composition 124 reacts to form a water-based zein composition 190, which is removed from the reactor for use in coatings and other end-use applications, for example, as described herein.

In some embodiments, the water-based prolamin compositions of the invention typically have a pH of about 7 or less (i.e., an acidic pH) due to the presence of the acid. In many embodiments, the pH of the water-based prolamin composition is about 6 or less; or about 5 or less; or about 4 or less. In an exemplary embodiment, the pH of the composition ranges from about 2 to about 4.

In some embodiments, the water-based prolamin compositions of the invention typically have a viscosity of about 7000 cps or less.

In some embodiments, the water-based prolamin compositions of the invention in the form of emulsions have a particle size that is less than about 25 microns, for example, about 20 microns or less.

Applications

The water-based prolamin compositions of the invention may be useful in a variety of applications such as those where water-based polymeric materials (e.g., acrylic latex or water-based polyurethanes) have typically been used. Examples include binders for surface coatings such as paints, clear coatings (e.g., varnishes), and printing inks. The water-based polymeric materials may also be used as binders or surface coatings for nonwoven fabrics, paper, paper products, and the like. The water-based zein compositions of the invention may also be used in adhesive compositions, for example, wood glue, paperboard adhesive, laminating adhesive, and the like. Additional examples include coatings for cans, eatable casings, pharmaceutical coatings, and the like. In some embodiments, the water-based zein compositions of the invention are suitable for use as food coatings, for example, coatings on vegetables, nuts, and seeds.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by the embodiments described by the language of the claims and the equivalents of those embodiments.

EXAMPLES

Example 1

Preparation of Zein Solution

A water-based zein composition of the invention was prepared as follows. 136 grams of 200 proof ethanol and 50 grams of distilled water were added to a flask and combined. Next, 20 grams of citric acid was added to the flask and the resulting acidified solvent composition was stirred until clear. The acidified solvent composition was heated and 20 grams of zein composition ($\alpha$-zein content of 85% weight and a $\beta$ and $\gamma$-zein content of 15% weight) was slowly added to the acidified solvent composition while stirring and heating. After addition of the zein, the resulting composition appeared bright yellow in color. The composition was then distilled to remove ethanol. Approximately 170 ml of distillate was removed at a temperature of about 79 to 88° C. The composition was cooled to provide a water-based zein composition in the form of a solution.

Example 2

Preparation of Zein Emulsion

A water-based zein composition of the invention was prepared as follows. 150 grams of 200 proof ethanol and 111 grams of distilled water were added to a flask and combined. Next, 20 grams of citric acid was added to the flask and the resulting acidified solvent composition was stirred until clear. The acidified solvent composition was heated and 20 grams of zein composition ($\alpha$-zein content of 85% weight and a $\beta$ and $\gamma$-zein content of 15% weight) was slowly added to the acidified solvent composition while stirring and heating. After addition of the zein, the resulting composition appeared bright yellow in color. The composition was then distilled to remove ethanol. When the composition turned bright yellow to opaque, the heat source was removed to end the distillation. Approximately 196 to 200 ml of distillate was removed at a temperature of about 83 to 95° C. The composition was stirred while cooling to provide a water-based zein composition in the form of an emulsion. The emulsion may settle and may need to be agitated periodically for the first several days after making to in order for the emulsion to stay suspended.

Examples 3-14

Examples 5-8 and 10 were prepared generally as described in Example 1 using the ingredient amounts shown in TABLE 2. Examples 3-4, 9, and 11-14 were prepared generally as described in Example 2 using the ingredient amounts shown in TABLE 2.

TABLE 2

| Example | State of material | Zein (g) | Citric acid (g) | 200 Proof Ethanol (g) | Water (g) | Percent Ethanol (w/w) | Final solids concentration | Viscosity (cps) |
|---|---|---|---|---|---|---|---|---|
| 1 | Solution | 20 | 20 | 136 | 50 | 73.1 | 57.8 | 1478 |
| 2 | Emulsion | 20 | 20 | 150 | 111 | 57.5 | 35.8 | 225 |
| 3 | Emulsion | 15 | 15 | 150 | 111 | 57.5 | 31.5 | 50 |
| 4 | Emulsion | 20 | 15 | 150 | 111 | 57.5 | 36.5 | 375 |
| 5 | Solution | 15 | 15 | 136 | 50 | 73.1 | 40.2 | 510 |
| 6 | Transition phase | 20 | 20 | 136 | 80 | 62.9 | 36.4 | 97 |
| 7 | Solution | 20 | 15 | 136 | 50 | 73.1 | 44.2 | 2310 |
| 8 | Solution | 25 | 25 | 136 | 50 | 73.1 | 58.1 | 970 |
| 9 | Emulsion | 25 | 25 | 150 | 111 | 57.5 | 41.5 | 405 |
| 10 | Solution | 25 | 25 | 136 | 50 | 73.1 | 58.1 | 4100 |
| 11 | Emulsion | 25 | 25 | 150 | 111 | 57.5 | 41.5 | 204 |
| 12 | Emulsion | 30 | 20 | 150 | 111 | 57.5 | 41.4 | 3800 |
| 13 | Emulsion | 35 | 20 | 150 | 111 | 57.5 | 40.0 | 4167 |
| 14 | Emulsion | 40 | 20 | 150 | 111 | 57.5 | 45.0 | 6900 |

Note:
Examples 10-14 were vacuumed distilled

Example 15

Preparation of Zein Solution Using HCl

A water-based prolamin composition of the invention was prepared as follows. 136 grams of 200 proof ethanol and 50 grams of distilled water were added to a flask and combined. Next, the pH was lowered to about 3 by adding 6 N hydrochloric acid to the flask and the resulting acidified solvent composition was stirred until clear. Next, 20 grams of zein (15.77% β-zein and γ-zein and 84.33% α-zein) was slowly added to the acidified solvent composition while stirring. After addition of the zein, the resulting composition appeared bright yellow in color and the pH increased. Additional 6 N hydrochloric acid was added to the acidified zein composition to reduce the pH to about 3. A total of 1.875 mL 6 N hydrochloric acid was added. The composition was then distilled to remove alcohol. Approximately 140 ml of distillate was removed at a temperature of about 77-78.5° C. The composition was stirred until cool to provide a water-based zein composition in the form of a solution.

Example 16

Preparation of Zein Emulsion Using HCl

A water-based prolamin composition of the invention was prepared as follows. 150 grams of 200 proof ethanol and 111 grams of distilled water were added to a flask and combined. Next, the pH was lowered to about 3 by adding 2 mL 6 N hydrochloric acid to the flask and the resulting acidified solvent composition was stirred. 20 grams of zein (15.77% β-zeins and γ-zeins and 84.33% α-zeins) was slowly added to the acidified solvent composition while stirring. After addition of the zein, the resulting composition appeared bright yellow in color and the pH increased. More 6 N hydrochloric acid was added to the acidified zein composition to reduce the pH to 3. A total of 2 mL 6 N hydrochloric acid was added. The composition was then distilled to remove alcohol. Approximately 179 ml of distillate was removed at a temperature of about 81-95° C. until the contents of the flask turned opaque at which time the flask was removed from the heat source. The composition was stirred until cool to provide a water-based zein composition in the form of an emulsion. The emulsion may settle and may need to be agitated periodically for the first several days after making to in order for the emulsion to stay suspended.

Example 17

Preparation of Gliadin Emulsion

A water-based prolamin composition of the invention was prepared as follows. Gliadin was extracted from vital wheat gluten using 70% (w/w) aqueous ethanol at 70° C. On a dry basis approximately 13.1 g of crude protein was extracted. Distilled water was then added to bring the concentration of ethanol in the extract equivalent to that used in Example 2. The ratio of protein to solvent is lower than in Example 2 because this is all that can be extracted under these conditions. Next, 15.6 g citric acid was added to the flask and the resulting acidified solvent composition was stirred.

After addition of the acid, the resulting composition appeared dark orange in color. The composition was then distilled to remove alcohol. Approximately 206 ml of distillate was removed at a temperature of about 77-85° C. (The contents of the flask did not turn opaque) at which time the flask was removed from the heat source. The composition was stirred until cool to provide a water-based gliadin composition in the form of an emulsion. The emulsion may settle and may need to be agitated periodically for the first several days after making to in order for the emulsion to stay suspended.

Preparation of Paper Using Water-Based Zein as Binder

Examples 1-7 were added as a binder at about 30% weight to 60 g/m² sheet of polyester synthetic fiber. Hand sheets (TAPPI method T205; 6 by 6 inch sheet) were prepared using a Euclid Size Press Coater. The samples were dried using a convection oven at 63° C. The hand sheets were tested for tensile strength and burst using TAPPI methods T404 and T403, respectfully. The hand sheets were compared to sheets that were prepared in the same manner using a commercial acrylic binder (Rhoplex B-15J). The results of the testing are shown in TABLE 2. As shown in TABLE 3, the properties of the hand sheets prepared with the water-based zein composition compared favorably to the hand sheets prepared using the acrylic binder.

TABLE 3

| Sample (Binder) | Basis weight (g/m2) | Binder (%) | Tensile Strength (KG/15 mm) | Burst (psig) |
|---|---|---|---|---|
| Control (No binder used) | 60 | 0 | 1.7 | 6 |
| 1 | 86 | 30 | 7.5 | 74 |
| 2 | 83 | 28 | 6.6 | 68 |
| 3 | 86 | 30 | 7.4 | 72 |
| 4 | 84 | 29 | 7.6 | 68 |
| 5 | 85 | 30 | 7.6 | 69 |
| 6 | 84 | 29 | 6.2 | 69 |
| 7 | 86 | 31 | 7.6 | 68 |
| Acrylic Binder (Rhoplex B-15J) | 85 | 30 | 7.6 | 83 |

Preparation and Testing of a Paint Composition Based on Water-Based Zein Composition Examples 10 and 11 from TABLE 1 were mixed together in equal parts to form a binder mixture. Next, 25 grams of the binder mixture was combined with 1.25 grams of $TiO_2$ and 0.025 grams of xanthan gum. The resulting paint formulation was applied to washed 5 by 7 inch pieces of 10 mil aluminum sheet material. The coatings on the sheet material were formed using an Accu-Lab Drawdown Machine that was equipped with a number 36 drawn down rod. The number 36 rod was used to form a 0.036 inch wet coating thickness for the paints. Using the same coating technique and sheet material, painted samples of a commercial paint formulation (acrylic latex paint from Valspar, Inc. of Minneapolis, Minn.) were also prepared for comparative testing purposes.

The paint prepared using Examples 10 and 11 was compared to a commercial paint for adhesion (Elcometer Adhesion), tension (Gardner Lab Mar), and hardness/scratch (Gardner-Hoffman). The testing showed that the paint containing a water-based zein binder compared favorably to the commercial paint formulations. The results of the testing are shown in TABLE 4.

TABLE 4

| Test instrument | Commercial Paint (Valspar, Inc.) | Water-based Zein Paint |
|---|---|---|
| Elcometer (psig) | 0.8 | 1.1 |
| Gardner Lab Mar (tension) | 2.5 | 2.5 |
| Gardner Hoffman Hardness (g) | 1000 | 1000 |
| Gardner Hoffman Scratch (g) | 400 | 600 |

Other embodiments of the invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

What is claimed is:

1. A method of making a water-based, flowable zein composition for delivering a zein, comprising:
   (A) providing an acidified zein composition comprising
      i. a zein comprising α-zein and at least one of β-zein and γ-zein in a total amount of at least about 15% by weight;
      ii. water;
      iii. at least one of alcohol and ketone; and
      iv. acid; and
   (B) removing at least a portion of the at least one of alcohol and ketone from the acidified zein composition to form a water-based, flowable zein composition comprising water in an amount ranging from at least about 30% by weight to at least about 75% by weight.

2. The method of claim 1, wherein the zein comprises α-zein, β-zein, and γ-zein.

3. The method of claim 1, wherein the water-based zein composition is a solution.

4. The method of claim 3, wherein the zein comprises about 15% to about 44% weight combined β-zein and γ-zein.

5. The method of claim 3, wherein the zein comprises about 15% to about 17% weight combined β-zein and γ-zein.

6. The method of claim 1, wherein the water-based zein composition is an emulsion.

7. The method of claim 6, wherein the zein comprises about 56% to about 88% weight α-zein, and about 15% to about 44% weight combined β-zein and γ-zein.

8. The method of claim 6, wherein the zein comprises about 75% to about 85% weight α-zein, and about 15% to about 25% weight combined β-zein and γ-zein.

9. The method of claim 1, wherein providing an acidified zein composition comprises:
   (1) providing a zein composition comprising:
      the zein, the at least one of an alcohol and ketone; and water; and
   (2) combining the zein composition with an acid to form the acidified zein composition.

10. The method of claim 9, wherein providing the zein composition comprises:
    (A) providing a solvent composition comprising: at least one of alcohol and ketone, and water;
    (B) combining the solvent composition with the zein to form the zein composition.

11. The method of claim 10, wherein combining the solvent composition with the zein further includes heating the solvent composition while the zein and solvent composition are being combined.

12. The method of claim 9, wherein providing a zein composition comprises:
    (A) providing a composition comprising: at least one of alcohol and ketone; water; distillers' grain; and, optionally a reducing agent;
    (B) extracting prolamin from the distillers' grain to provide an extracted composition comprising prolamin, at least one of alcohol and ketone, and water; and
    (C) separating the distillers' grain from the extracted composition to provide the zein composition.

13. The method of claim 1, wherein providing an acidified zein composition comprises:
    (A) providing an acidified solvent composition comprising: at least one of alcohol and ketone; water; and an acid; and (B) combining the acidified solvent composition with the zein to form the acidified zein composition.

14. The method of claim 13, further comprising heating the acidified solvent composition while the zein and acidified solvent composition are being combined.

15. The method of claim 1, wherein removing comprises distilling the at least one of alcohol and ketone from the acidified zein composition.

16. The method of claim 15, wherein the distillation comprises vacuum distillation.

17. The method of claim 1, wherein the acid comprises an organic acid, an inorganic acid, or a mixture thereof.

18. the method of claim 17, wherein the organic acid is a carboxylic acid selected from acetic acid, lactic acid, formic acid, propionic acid, glycolic acid, D-gluconic acid, and L-ascorbic acid, citric acid, malic acid, levulinic acid, tartaric acid, succinic acid, glutaric acid, isocitric acid, aconitic acid, propane 1,2,3-tricarboxylic acid, and mixtures thereof.

19. The method of claim 17, wherein the inorganic acid comprises hydrochloric acid (HCl).

20. The method of claim 1, wherein the at least one alcohol and ketone is selected from methanol, ethanol, 1-propanol, 2-propanol, butanol (e.g., t-butanol), acetone, and mixtures thereof.

21. The method of claim 1, wherein the water-based zein composition comprises about 35% weight or less of at least one of alcohol and ketone.

22. The method of claim 1, wherein the water-based zein composition comprises about 8% weight prolamin or greater.

23. The method of claim 1, wherein the water-based zein composition comprises about 15% to about 35% weight zein; about 30% to about 75% weight water; about 0.1% to about 35% weight acid; and about 3% weight to about 35% weight combined alcohol and ketone.

24. The method of claim 1, wherein the water-based zein composition has a pH of about 7 or less.

25. The method of claim 1, wherein the water-based zein composition has a pH of about 2 to about 4.

* * * * *